United States Patent
Hwu et al.

(10) Patent No.: US 9,799,479 B2
(45) Date of Patent: Oct. 24, 2017

(54) METHOD, SYSTEM, AND LIGHT SOURCE FOR PENETRATING RADIATION IMAGING

(71) Applicant: Academia Sinica, Taipei (TW)

(72) Inventors: Yeu-Kuang Hwu, New Taipei (TW); Tsung-Tse Li, Taipei (TW); Yu-Tai Ching, Hsinchu (TW)

(73) Assignee: ACADEMIA SINICA (TW)

( * ) Notice: Subject to any disclaimer, the term of this patent is extended or adjusted under 35 U.S.C. 154(b) by 78 days.

(21) Appl. No.: 14/612,393

(22) Filed: Feb. 3, 2015

(65) Prior Publication Data
US 2015/0228440 A1 Aug. 13, 2015

(30) Foreign Application Priority Data

Feb. 11, 2014 (TW) .............................. 103104385 A

(51) Int. Cl.
| | |
|---|---|
| H01J 35/08 | (2006.01) |
| H01J 35/30 | (2006.01) |
| G06T 11/00 | (2006.01) |
| A61B 6/00 | (2006.01) |
| G01N 23/04 | (2006.01) |
| G01N 23/20 | (2006.01) |

(52) U.S. Cl.
CPC .............. *H01J 35/08* (2013.01); *A61B 6/40* (2013.01); *G06T 11/006* (2013.01); *H01J 35/30* (2013.01); *A61B 6/5205* (2013.01); *G01N 23/04* (2013.01); *G01N 23/20075* (2013.01); *H01J 2235/086* (2013.01)

(58) Field of Classification Search
CPC .......... A61B 6/00; A61B 6/40; A61B 6/4021; A61B 6/52; A61B 6/5205; H01J 1/00; H01J 1/02; H01J 1/36; H01J 1/38; H01J 35/00; H01J 35/02; H01J 35/04; H01J 35/08; H01J 35/30; H01J 2201/00; H01J 2235/00; H01J 2235/08; H01J 2235/081; H01J 2235/086; G06T 5/00; G06T 5/001; G06T 5/003; G06T 11/00; G06T 11/003; G06T 11/006; H04N 1/04; H04N 5/30; H04N 5/32; H04N 5/335

See application file for complete search history.

(56) References Cited

U.S. PATENT DOCUMENTS

2004/0184675 A1* 9/2004 Brown .................... G06T 5/003
382/279

OTHER PUBLICATIONS

Shimura, Takayoshi, et al., "Hard X-ray Phase Contrast Imaging Using a Tabletop Talbot-Lau Interferometer with Multiline Embedded X-ray Targets", Jan. 9, 2013, Optical Society of America, Optics Letters, vol. 38, No. 2, pp. 157-159.*

(Continued)

*Primary Examiner* — Anastasia Midkiff
(74) *Attorney, Agent, or Firm* — Bacon & Thomas, PLLC

(57) ABSTRACT

The present invention relates to a method, a system, and a light source for penetrating radiation imaging, and more particularly, to a method, a system, and a light source for X-ray imaging. The system for X-ray phase contrast and high resolution imaging of the present invention comprises an X-ray source comprising a plurality of X-ray micro-light sources, an X-ray sensor configured to receive X-rays penetrating an object, and a computer configured to receive and compute raw image data from the X-ray sensor so as to obtain a clear image of the object.

13 Claims, 5 Drawing Sheets

(56) References Cited

OTHER PUBLICATIONS

Olivo, A., et al., "Deconvolution of X-ray Phase Contrast Images as a Way to Retrieve Phase Information Lost Due to Insufficient Resolution", Jul. 10, 2009, Institute of Physics and Engineering in Medicine, Physics in Medicine and Biology, vol. 54, pp. N347-N354.*

* cited by examiner

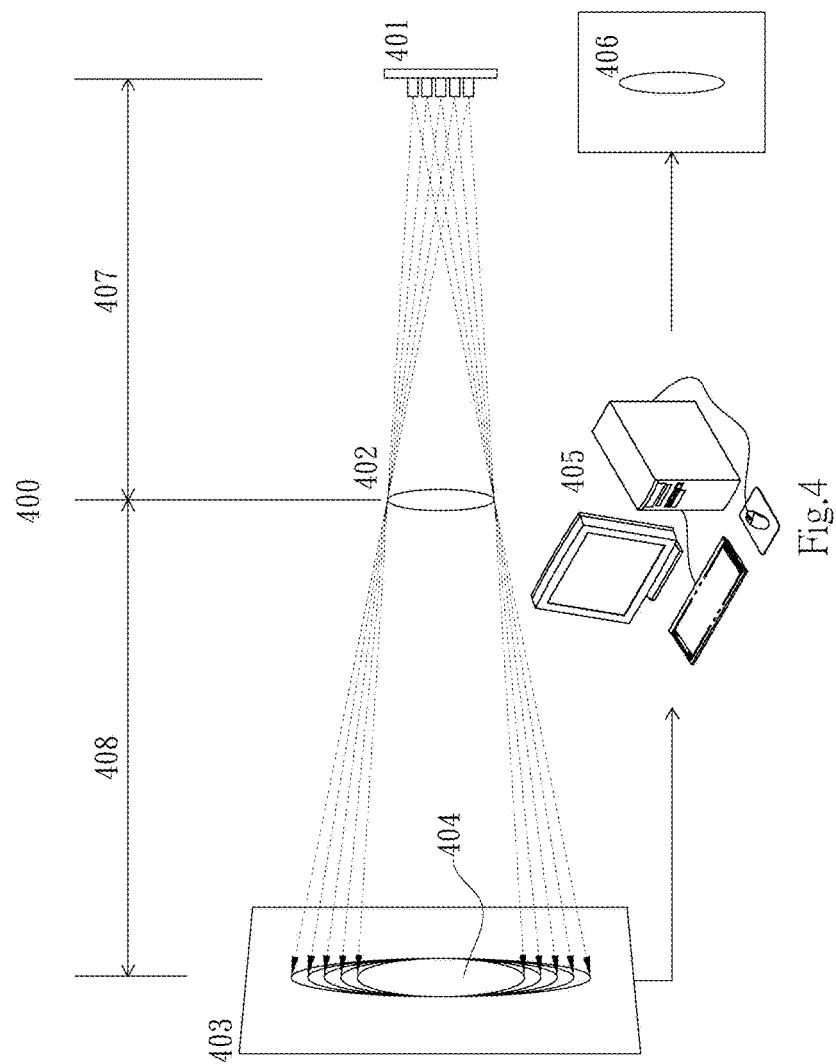

METHOD, SYSTEM, AND LIGHT SOURCE FOR PENETRATING RADIATION IMAGING

BACKGROUND OF THE INVENTION

1. Field of the Invention

The present invention relates to a method, a system and a light source for penetrating radiation imaging, and more particularly, to a method, a system and a light source for X-ray imaging.

2. Description of Related Art

X-ray and visible light have similar wave properties, that is, they both exhibit diffraction and interference phenomena. For X-ray imaging, diffraction and interference phenomena can enhance the contrast of an image, edges of the image in particular. Such a contrast enhancement results from different real parts of refractive indices of various materials. The interfaces between various materials in an imaged object correspond to edges in the image so that the contrast at the edges is enhanced, and this is called phase contrast edge enhancement. In comparison with the conventional X-ray radiography that causes X-ray to penetrate a sample and creates an image contrast on an X-ray film according to different amounts of X-ray absorbed by various parts of the sample (concerning the imaginary part of the refractive index), X-ray phase contrast imaging has the potential to significantly enhance the image contrast and resolution. Moreover, X-ray phase contrast imaging can be used with the conventional X-ray radiography to improve the image quality. On the other hand, regarding medical images, the conventional X-ray radiography displays poor performance in imaging soft tissues because soft tissues absorb relatively small amounts of X-ray and thus the images thereof lack absorption contrast. Therefore, X-ray phase contrast imaging can compensate the conventional X-ray photography's deficiency in imaging soft tissues.

Synchrotron X-ray sources characterized by coherence, collimation and high power density have been proved to favorably facilitate the implementation of X-ray phase contrast imaging. However, bulky volumes and high manufacturing costs all prevent synchrotron X-ray sources from being widely applied X-ray phase contrast to medical imaging involve human. The X-ray source for the conventional X-ray radiography generates X-ray by directing a high-energy electron beam to a metal target, but it can hardly create the phase contrast edge enhancement effect due to the following reasons. First of all, it is not easy for light emitting spots of a conventional X-ray source to form a small spot light source because of the damage to the metal target (the high temperature at the spot where energy is accumulated causes the metal to melt or vaporize) caused by the high-energy electron beam, thus for most of applications the X-ray source is configured in large scale as an extended source whose spot size determines the resolution of the X-ray image. Insufficient resolution will weaken the edge enhancement caused by the phase contrast at the interfaces between different materials. As a result, the image merely remains an identifiable differentia caused by X-ray absorbency but with low resolution, where the phase contrast effect is erased. Lastly, compared with the synchrotron X-ray source, the conventional X-ray source has a high divergence, and an X-ray optical system with a large f-number is required to increase the intensity of the X-ray incident to the sample. Such an optical system with a large f-number has fairly low feasibility and thus cannot be used to improve or solve the problem of low resolution and thereby to perform phase contrast imaging.

Theoretically, a plate with a pinhole can be used to filter out the majority of X-rays with only a small portion of X-rays passing through the holes being used to form images so as to boost the functionality of the conventional X-ray source and thereby to perform phase contrast imaging. However, this approach could greatly reduce the intensity of the light source as well as the received signal and results in a lengthy period of time for capturing images, thus it is inapplicable in producing medical images (a natural movement by a patient being photographed may cause a blurred image). Moreover, increasing the intensity of the X-ray before the filtering to increase the intensity of the X-ray passing through the holes also has certain limitation because the overall intensity of the X-ray source for a conventional metal target is subject to the extent of damage to the metal target caused by a bombardment of massive electrons.

Micro-focused X-ray source employs a focused electron beam to hit the metal target. Such a light source can create sufficient phase contrast, but it has a material drawback of a dramatically reduced luminance. In consideration of the damage to the metal target caused by a bombardment of massive electrons, it proved to be quite difficult to generate high flux X-rays by bombarding the metal target with a focused electron beam without damaging (melting) the target. Therefore, applying a micro-focused X-ray source to phase contrast imaging requires a lengthy period of time to form images as well.

Another practical approach for improving the conventional X-ray source's (not an accelerator based light source) efficiency in phase contrast imaging utilizes a grating interferometer. However, this approach requires a multi-image scanning and the sequential image reconstruction, and thus will experience difficulties when being used to form X-ray images of a living body. In addition, the resolution of images created by this approach is limited by the precision of the gratings. The grating interferometer for medical phase contrast imaging requires gratings with large areas and high precision, and it is rather difficult to meet these technical requirements.

To sum up, in spite of excellent imaging performance, X-ray phase contrast imaging's range of application and popularity are restricted by the light source and the corresponding imaging system. Therefore, a need exists in the art for an X-ray source characterized by simplicity, low cost, phase contrast and sufficient power density and meeting the requirements of high resolution medical images and a shortened imaging process.

SUMMARY OF THE INVENTION

In order to improve the image quality of penetrating radiation imaging and to shorten the imaging process to satisfy the requirements of medical images, the present invention provides a light source for penetrating radiation imaging including: a plurality of penetrating radiation micro-light sources distributed at different known spatial locations to irradiate an object, thereby generating a raw image consisting of superimposed images of the object generated by the illumination of each micro-light source.

The present invention further provides a system for penetrating radiation imaging including: the foregoing light source for penetrating radiation imaging configured to generate a penetrating radiation to irradiate an object; a sensor configured to receive the penetrating radiation that penetrates the object; and a computer receiving and computing raw image data from the sensor to obtain a clear image of the object.

Preferably, in the system for penetrating radiation imaging of the invention, the computation of the raw image data by the computer comprises performing deconvolution on the raw image data by utilizing distribution information associated with the known locations of the plurality of penetrating radiation micro-light sources so that the superimposed images can coincide with each other.

The present invention further provides a method for penetrating radiation imaging including: irradiating an object with a penetrating radiation generated by the foregoing light source for penetrating radiation imaging of the present invention; receiving, by a sensor, the penetrating radiation penetrating the object; and receiving and computing, by a computer, raw image data from the sensor to obtain a clear image of the object.

The present invention further provides an X-ray source for X-ray imaging including: a plurality of X-ray micro-light sources, wherein the plurality of X-ray micro-light sources are distributed at different known spatial locations to irradiate an object, thereby obtaining a raw image consisting of superimposed images of the object.

The invention further provides an X-ray source for X-ray imaging that includes an electron gun configured to generate an electron beam; a plate; and a plurality of metal micro-targets arranged into an array on a surface of the plate; wherein the electron beam hits a portion or all of the plurality of metal micro-targets to generate X-rays.

Preferably, in the X-ray source of the present invention, a spacing between any two adjacent metal micro-targets of the plurality of metal micro-targets ranges from 50 μm to 200 μm.

Preferably, in the X-ray source of the present invention, the X-rays are collected at one side of the plate to which the electron beam is incident.

Preferably, in the X-ray source of the present invention, the X-rays are collected the other side of the plate opposite to the side to which the electron beam is incident.

The present invention further provides an X-ray source for X-ray imaging that includes an electron gun configured to generate an electron beam; and a metal target; wherein the electron beam scans over various parts of the metal target so as to generate X-rays at different spatial locations correspondingly.

Preferably, in the X-ray source of the present invention, the electron beam completes a scanning cycle within a period of time of less than 1 second.

The present invention further provides a system for X-ray imaging including: the foregoing X-ray source configured to generate X-rays to irradiate an object; an X-ray sensor configured to receive the X-rays penetrating the object; and a computer configured to receive and compute raw image data from the X-ray sensor to obtain a clear image of the object.

Preferably, in the system for X-ray imaging of the present invention, a distance between the object and the X-ray sensor ranges from 10 centimeters to 1 meter.

Preferably, in the system for X-ray imaging of the present invention, the raw image data is image data associated with a blurred image consisting of superimposed images of the object.

Preferably, in the system for X-ray imaging of the present invention, the computation of the raw image data by the computer includes deconvolution on the raw image data by utilizing distribution information associated with the known locations of the plurality of X-ray sources so that the superimposed images can coincide with each other.

Preferably, in the system for X-ray imaging of the present invention, the X-ray sensor is capable of performing pixel displacement to synchronously correspond to the spatial and temporal locations of the X-ray light sources so that the superimposed images can coincide with each other.

The present invention further provides a method for X-ray imaging that includes irradiating an object with the foregoing X-ray source of the present invention; receiving, by an X-ray sensor, X-rays penetrating the object; and receiving and computing, by a computer, raw image data from the X-ray sensor to obtain a clear image of the object.

BRIEF DESCRIPTION OF THE DRAWINGS

The present description will be better understood from the following detailed description read in light of the accompanying drawings, where:

FIG. 4 illustrates a system for X-ray imaging of the present invention;

DESCRIPTION

Figure 1:
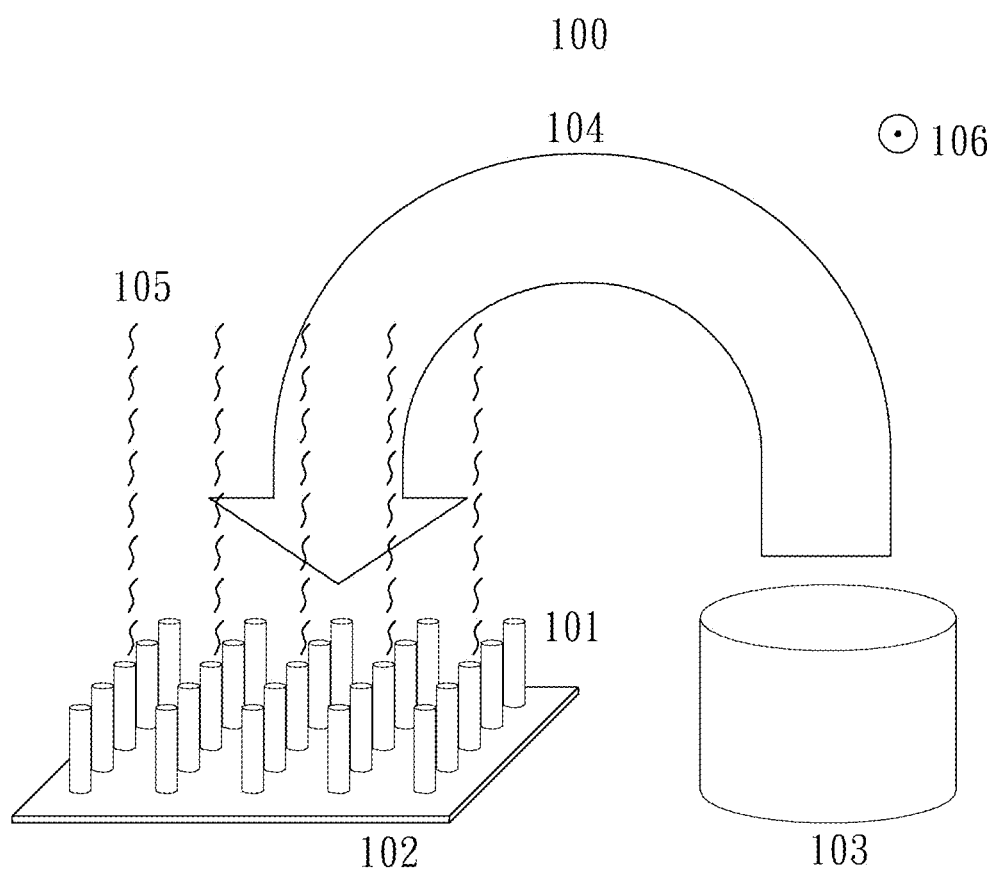
FIG. 1 illustrates an X-ray source for X-ray imaging of the present invention.

The present invention will be described fully with reference to the accompanying drawings provided with preferred embodiments of the invention, but it will be understood, prior to this description, that modifications to the invention described herein may be made by a person skilled in the art while the functions of the invention can be achieved. Therefore, it will be understood that the following description is a general disclosure to a person skilled in the art and the content thereof is not intended to limit the present invention.

Details of the objects, technical configuration, and effects of the present invention will be described more fully hereinafter with reference to the accompanying drawings, in which exemplary embodiments of the invention are shown. The like reference numerals indicate the like configuration throughout the specification, and in the drawings, the length and thickness of layers and regions may be exaggerated for clarity. The technical content of the present invention will become apparent by the detailed description of the following embodiments and the illustration of related drawings as follows. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Various embodiments will now be described more fully with reference to the accompanying drawings, in which illustrative embodiments are shown. The inventive concept, however, may be embodied in various different forms, and should not be construed as being limited only to the illustrated embodiments. Rather, these embodiments are provided as examples, to convey the inventive concept to one skilled in the art. Accordingly, known processes, elements, and techniques are not described with respect to some of the embodiments.

The singular forms "a", "and", and "the" are used herein to include plural referents unless the context clearly dictates otherwise.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art.

The present invention relates to penetrating radiation imaging, and more particularly, to a light source, a method and a system for X-ray imaging. The method and the system for X-ray imaging utilize an X-ray source of the present invention, which includes a plurality of X-ray micro-light sources distributed at different spatial locations to irradiate an object. When the object is imaged with such an X-ray source, the raw image thereof will be a blurred image consisting of multiple superimposed similar images slightly offset from each other on the imaging surface (i.e. the sensor). When the X-ray source's design satisfies certain requirements, such a blurred image may be approximate to an ideal image, a result of spatial convolution on the imaging surface. Thus, the approximate ideal image can be restored with deconvolution through image processing. The restoration process is equivalent to aligning respective superimposed images and performing the addition of signals, through which the signal to noise ratio (SNR) is increased and the image details (i.e. the enhanced edges) can be restored accordingly.

In this X-ray phase contrast imaging system, each of the plurality of X-ray micro-light sources is approximate to a spot light source and thus capable of generating high resolution images and creating phase contrast. That is, the smaller the area of each of the plurality of X-ray micro-light sources, the more the X-ray micro-light source is approximate to a spot light source. An image (one of multiple superimposed images) formed by a single X-ray micro-light source as a light source exhibits a significantly increased resolution and a strong phase contrast edge enhancement effect. However, in order to reduce the time required for capturing images, each of the plurality of X-ray micro-light sources must have a certain light-emitting area so as to obtain a sufficient signal intensity to overcome noise interference. In addition to increasing the light-emitting area of each individual micro-light source, the total number of X-ray micro-light sources can also be increased to enhance the overall luminance of the X-ray source. For example, a 100×100 array of X-ray micro-light sources can shorten the time required for capturing images by ten thousand (10,000) times.

In the X-ray source of the present invention, each of the plurality of X-ray micro-light sources does not rely on a particular method for generating X-rays. For example, accelerator based synchrotron radiation is not required in the present invention because whether each of the plurality of micro-light sources has sufficient capacity for high resolution or phase contrast imaging mainly depends on the micro light-emitting area thereof. Thus, the conventional X-ray source that generates X-rays by hitting the metal target with an electron beam is applicable to high resolution and phase contrast imaging if configured according to the method provided by the present invention. The X-ray source of the present invention can solve the following problems. Firstly, the creation of phase contrast is based on the micro light-emitting area of the light source, and thus each of the superimposed images on the imaging surface shows the edge enhancement effect. Secondly, although the raw image is a blurred image consisting of superimposed images, most of the edge enhancement information is retained (only the position requires adjustment) due to the separation of the micro-light sources with respect to each other. Therefore, the X-ray source of the present invention also minimizes the negative impact on phase contrast caused by a conventional extended X-ray source. Lastly, the arrangement of a plurality of micro-light sources enables the overall power (luminance) of the extended X-ray source to be adjusted so that the X-ray source of the present invention has the potential to be applied to medical imaging. On the one hand, the X-ray phase contrast imaging is advantageous for soft tissue imaging. On the other hand, the dose of radiation exposure to the patient can be reduced because of a relatively high image quality (contrast in particular) in phase contrast imaging, that is, less amount of X-rays are required to achieve the image quality similar to that achieved by the conventional X-ray imaging.

As described above, the X-ray source of the present invention includes a plurality of X-ray micro-light sources. The plurality of X-ray micro-light sources are generally arranged into an array, thus the light-emitting area of each of the plurality of micro-light sources, the spacing between any two adjacent micro-light sources and the total number of the micro-light sources are all taken into consideration for the design. It is to be noted that in the X-ray source of the present invention, the X-ray micro-light sources do not have to be coherent micro-light sources because the image formed by each of the plurality of micro-light sources retains its own edge enhancement information, so that the final step of image reconstruction does not rely on the effects of light source fluctuation.

FIG. 1 illustrates an X-ray source 100 for X-ray phase contrast imaging. In the X-ray source 100, a plurality of metal micro-targets 101 are distributed over a plate 102. An electron gun 103 is configured to generate an electron beam 104 which is deflected by a magnetic field 106 to be incident to the plurality of metal micro-targets 101. A plurality of X-rays 105 are then respectively generated at the plurality of metal micro-targets 101 bombarded by electrons of the electron beam, thereby realizing a plurality of X-ray micro-light sources. In this embodiment, the X-rays are collected at the side of the plate to which the electron beam 104 is incident.

Figure 2:
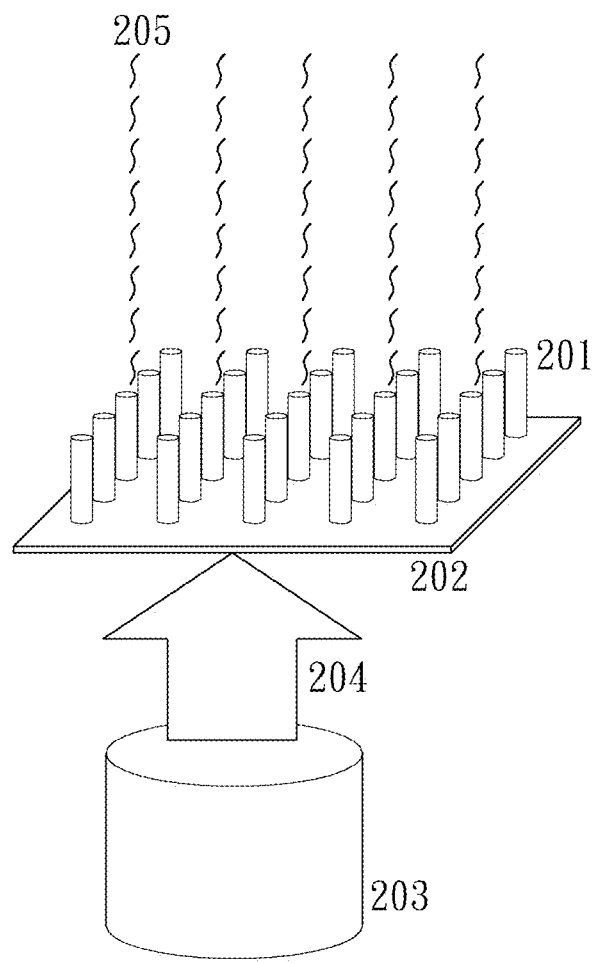
FIG. 2 illustrates another X-ray source for X-ray imaging of the present invention.

FIG. 2 illustrates another X-ray source 200 for X-ray phase contrast imaging of the present invention. In X-ray source 200, a plurality of metal micro-targets 201 are distributed over a plate 202. An electron gun 203 is configured to generate an electron beam 204 incident to the plurality of metal micro-targets 201. A plurality of X-rays 205 is then generated at the plurality of metal micro-targets bombarded by electrons of the electron beam, thereby realizing a plurality of X-ray micro-light sources. In this embodiment, the X-rays 205 are collected at the other side of the plate 202 opposite to the side to which the electron beam 204 is incident.

While the metal micro-target is a tiny column in the above embodiments, it is not limited to any shape or material (any metallic material capable of generating X-rays when bombarded by electrons is a potential option). The plurality of metal micro-targets are generally arranged into an array, but this is not essential for the present invention, that is, a linear arrangement or any other arrangement will not affect the nature of the present invention. In the above embodiments, much consideration is given to the cross-sectional area of an individual metal micro-target, the combined cross-sectional area of the plurality of metal micro-targets and the spacing between any two adjacent metal micro-targets. The cross-sectional area of the metal micro-target determines the degree of approximation between each micro-light source and a spot light source (which is in direct association with the coherence of each spot light source), as well as the luminance of each micro-light source. According to the experience, it is possible to attain a good balance between luminance and coherence for each micro-light source when a metal micro-target has a cross-sectional area ranging from about one hundred to ten thousand square micrometers (100-10000 $\mu m^2$). In the embodiments shown in FIG. 1 and FIG. 2, each of the metal micro-targets 101 and 201 has a circular cross-sectional area with a diameter of 20 µm.

As described above, the spacing between the any two metal micro-targets determines the discreteness among the plurality of metal micro-targets. That is, the larger the spacing, the more distantly the plurality of superimposed images in the raw image is distributed, and consequently, more edge enhancement information associated with each individual image will be reserved. However, an excessively large spacing also poses a negative impact. First of all, an excessively large spacing reduces the overall luminance of the light source and may lengthen the period of time required for capturing images. Moreover, it is likely that the scale of the entire light source will be increased (that is, the number of the targets remains unchanged while the spacing between the targets is increased) to compensate the loss of luminance caused by the excessively large spacing between the targets. Such an arrangement will increase the difficulty in manufacturing the entire light source device, and more significantly, the similarity between the superimposed individual images in the raw image will be destroyed due to a larger variation in the relative positions of the micro-light sources and the object to be imaged. Specifically, an illumination angle (with respect to the object) of each of the plurality of X-ray micro-light sources is slightly different from that of another micro-light source, thus the micro-light sources in an excessively discrete state would cause an excessive variation between the plurality of superimposed individual images in the raw image and makes it impossible to restore the raw image to an ideal image with details. The spacing between any two adjacent metal micro-targets may range from 50 µm to 200 µm according to different requirements for capturing images, including image details and the time required for capturing images. In the embodiments shown in FIG. 1 and FIG. 2, the spacing between two metal micro-targets is 100 µm.

Figure 3:
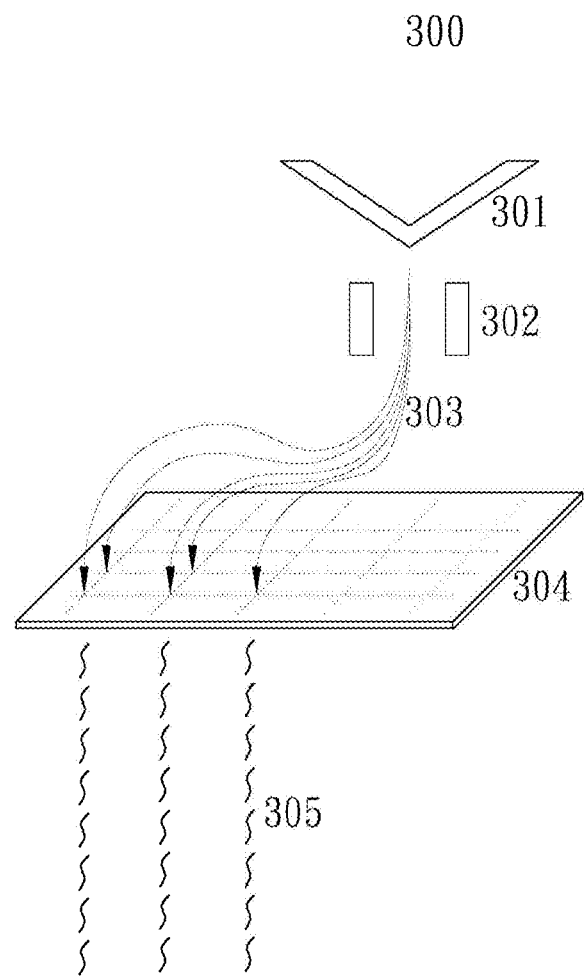
FIG. 3 illustrates yet another X-ray source for X-ray imaging of the present invention.

FIG. 3 illustrates another X-ray source 300 for X-ray phase contrast imaging of the present invention, which still employs a plurality of X-ray micro-light sources. The embodiment shown in FIG. 3 is different from the aforementioned two embodiments in that X-rays are generated at different spatial locations by means of scanning. As shown in FIG. 3, a pulsed electron source 301 is configured to generate an electron beam 303 which is directed to different locations at a metal target 304 by a scanning electrode 302. Thus, X-rays 305 can be generated at different locations, thereby realizing an X-ray source with a plurality of micro-light sources. In this embodiment, the X-rays are collected at the other side of the metal target 304 opposite to the side to which the electron beam 303 is incident. However, for an X-ray source with a plurality of micro-light sources realized by means of scanning, the X-rays can also be collected at the side of the metal target to which the electron beam is incident. As to other aspects to be taken into consideration for the design, such as the size of each of the plurality of micro-light sources or the spacing between any two adjacent micro-light sources, they are similar to those considered for the light sources shown in FIG. 1 and FIG. 2. The biggest difference between this embodiment employing the scanning technique and the aforementioned two embodiments is that consideration is given to the time required for capturing images. In systems for forming medical images or images of a living body, the restriction on the time required for capturing images should be taken into consideration. Obviously, a complete scanning cycle (during which the electron beam scans each predetermined location) must be shorter than the time required for capturing images. Generally, in the practice of medical imaging, the time required for capturing images needs to be controlled within 1 second. For the X-ray source shown in FIG. 3, a complete scanning cycle of the electron beam is 1 second or shorter.

FIG. 4 illustrates a system for X-ray imaging 400. In this embodiment, an X-ray source 401 similar to the one in FIG. 1 or FIG. 2 is provided. The X-ray source 401 comprises a plurality of linearly aligned X-ray micro-light sources and is configured to irradiate an object 402. An X-ray sensor 403 is configured to receive X-rays that penetrate the object 402, and the X-rays penetrating the object form a raw image 404. As the X-ray source 401 comprises the plurality of X-ray micro-light sources, the raw image 404 is a blurred image consisting of superimposed images of the object 402. It is to be noted that the raw image 404 contains not only information about edges enhanced by phase contrast imaging but also contrast information generated because of different amounts of X-ray absorbed by various materials (or different tissues). Consequently, the restored image also contains these information. As shown in FIG. 4, the raw image data detected by the X-ray sensor 403 is computed by a computer 405 and restored to a clear image 406. The computation mainly includes deconvolution so that the superimposed images can coincide with each other.

In the embodiment illustrated in FIG. 4, the distance 408 between the object 402 and the X-ray sensor 403 is a significant parameter for the system for X-ray imaging 400 and in direct association with the phase contrast information in the image. If the distance 408 is too short, different X-ray refraction effects created due to different refractive indices of various materials could not be presented, thus the phase contrast could not be created on the X-ray sensor 403 (or the phase contrast signal is too weak). If the distance 408 is too long, the refraction based phase contrast would be overly diffused on the imaging surface (i.e. the surface of the X-ray sensor 403) and, accordingly, causes a significant reduction in the contrast. As can be seen from the above description, there is an ideal value or an ideal range for the distance 408, and both of which are influenced by the refractive index of the object (inclusive of different refractive indices). Generally, the distance 408 is within a range between 10 centimeters to 1 meter. In FIG. 4, the distance 407 between the X-ray source 401 and the object 402 is determined by the image magnification (ratio of the image to the object). For example, in the system shown in FIG. 4, the distance 408 can be initially set to be 50 centimeters and, if an image magnification of 2× is required, it can be calculated from the geometric relationship that the distance 407 is also 50 centimeters.

When the distance 408 and the size of the metal micro-target satisfy the requirements for a good phase contrast and the spacing between any two adjacent metal micro-targets is not excessively large, each of the plurality of X-ray micro-light sources will form an individual phase contrast image of the object on the surface of the X-ray sensor 403. These individual images are extremely similar and thus the superimposed images (raw image 404) formed thereof can be deemed as an ideal image, a result of spatial convolution. Accordingly, the computer 405 can receive raw image data from the X-ray sensor 403, and perform deconvolution on such data based on information about the number of metal micro-targets, the array pattern, the spacing between any two adjacent metal micro-targets, the distances 407 and 408 in the X-ray source and etc. so as to adjust the location of each individual image in the superimposed images to correctly superimpose image signals, thereby improving the SNR of the image and restoring the image details to a clear image 406.

Figure 5A:
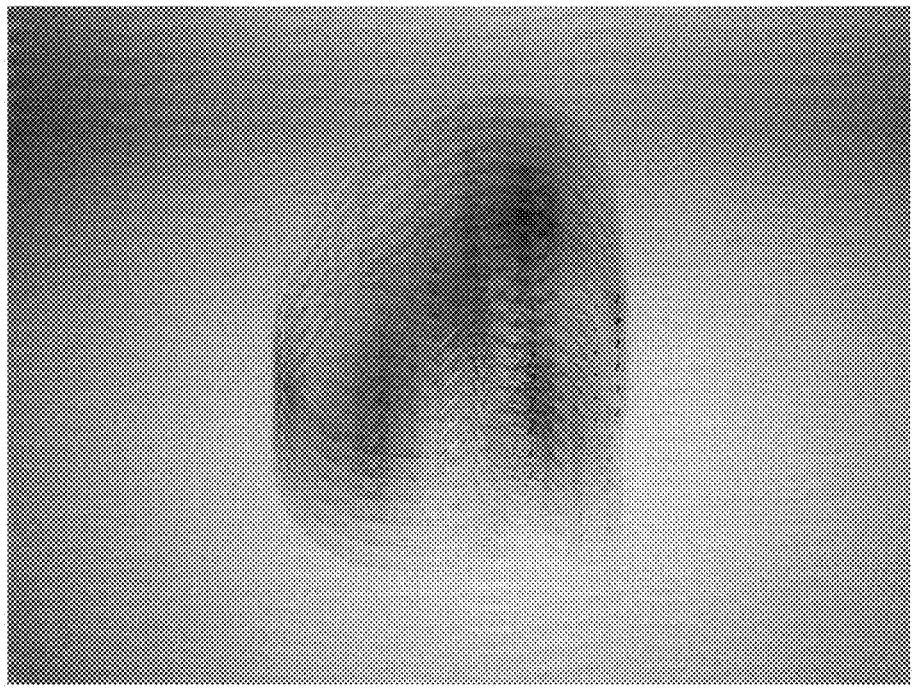
FIG. 5A illustrates a raw image of a sample photographed using the X-ray source and system of the present invention.
Figure 5B:
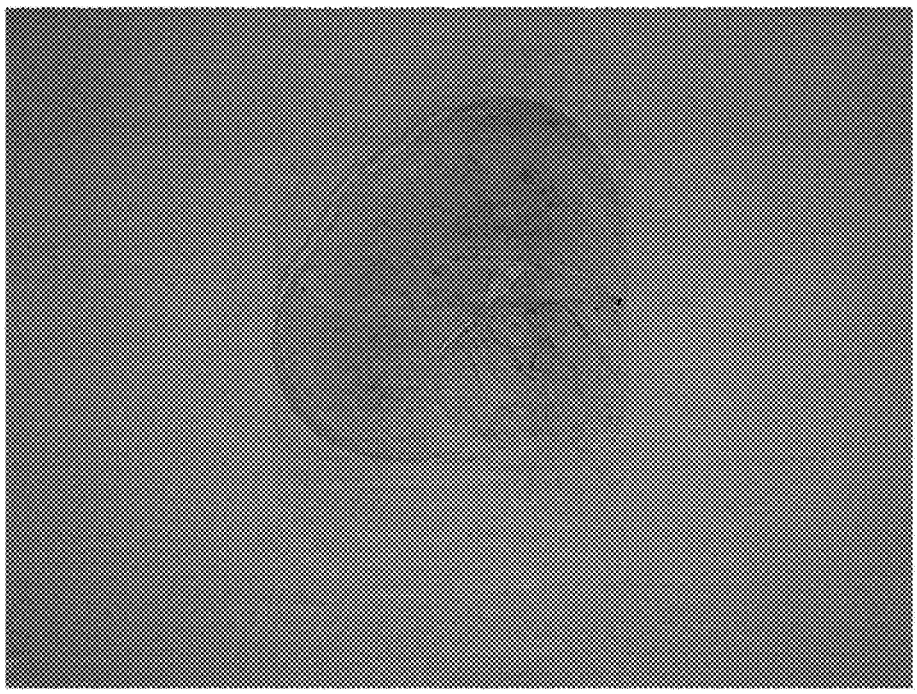
FIG. 5B illustrates a clear image obtained after the image consisting of superimposed images, as shown in FIG. 5A, has been processed.

FIG. 5A shows a raw image of a sample formed by using the system for X-ray imaging shown in FIG. 4. As the X-ray source 401 comprises a plurality of linearly X-ray micro-light sources, the raw image includes a plurality of vertically aligned individual images. FIG. 5B shows an image, which is the result of deconvolution performed on the raw image data shown in FIG. 5A. Image details produced by the phase contrast can be seen in FIG. 5B.

The embodiments of the present invention exemplify a number of X-ray sources characterized by simple configuration, low manufacturing cost, phase contrast and sufficient power density and meeting the requirements of high resolution medical images and an extremely short imaging process. The embodiments of the present invention also exemplify systems and methods for X-ray imaging corresponding to the foregoing X-ray sources so as to generate phase contrast X-ray images. The concept of using a plurality of micro-light sources to form a light source required for an imaging system to improve the image resolution is applicable to other systems for penetrating radiation imaging.

What is claimed is:

1. An X-ray source for X-ray imaging, comprising:
an electron gun configured to generate an electron beam;
a plate; and
a plurality of metal micro-targets distributed over a surface of the plate to form an array of metal micro-targets, and each of the plurality of the metal micro-targets being formed in the shape of a column extending from the surface of the plate;
wherein the electron beam hits a portion or all of the plurality of metal micro-targets on the plate to generate X-rays.

2. The X-ray source of claim 1, wherein a spacing between any two adjacent metal micro-targets of the plurality of metal micro-targets ranges from 50 μm to 200 μm.

3. The X-ray source of claim 1, wherein the X-rays are generated at a same side of the plate to which the electron beam is incident.

4. The X-ray source of claim 1, wherein the plate has a first side where the X-rays are generated and a second side opposite to the first side where the electron beam is received.

5. An X-ray source for X-ray imaging, comprising:
a plurality of X-ray micro-light sources distributed at different predetermined spatial locations to irradiate an object which is to be imaged by an X-ray sensor without one or more micro-patterned structures distributed between the object and the X-ray sensor, thereby generating a raw image consisting of superimposed images of the object,
wherein each of the plurality of X-ray micro-light sources is formed in the shape of a column extending along a direction substantially toward the object to be imaged.

6. The X-ray source of claim 5, wherein a spacing between any two adjacent X-ray micro-light sources of the plurality of X-ray micro-light sources ranges from 50 μm to 200 μm.

7. A system for X-ray imaging, comprising:
an X-ray source comprising an array of metal micro-targets configured to generate X-rays to irradiate an object;
an X-ray sensor configured to receive the X-rays penetrating the object without said x-rays being modified by one or more micro-patterned structures arranged between the object and the X-ray sensor; and
a computer configured to receive and compute raw image data from the X-ray sensor to obtain a clear image of the object without phase modulation of the x-rays received by the sensor.

8. The system of claim 7, wherein a distance between the object and the X-ray sensor ranges from 10 centimeters to 1 meter.

9. The system of claim 7, wherein the raw image data is image data associated with a blurred image consisting of superimposed images of the object.

10. The system of claim 9, wherein the computation of the raw image data by the computer comprises performing deconvolution on the raw image data by utilizing distribution information associated with distribution of the plurality of X-ray sources so that the superimposed images can coincide with each other.

11. A method for X-ray imaging, comprising:
irradiating an object with an X-ray source as recited in claim 1;
receiving, by an X-ray sensor, X-rays penetrating the object; and
receiving and computing, by a computer, raw image data from the X-ray sensor to obtain a clear image of the object by performing deconvolution on the raw image data based on information associated with the distribution of the plurality of X-ray sources.

12. The method of claim 11, wherein a distance between the object and the X-ray sensor ranges from 10 centimeters to 1 meter.

13. The method of claim 11, wherein the raw image data is image data associated with a blurred image consisting of superimposed images of the object.

* * * * *